US012628302B2

(12) United States Patent
Tan et al.

(10) Patent No.: US 12,628,302 B2
(45) Date of Patent: May 12, 2026

(54) ELECTRONIC DEVICE

(71) Applicant: HONOR DEVICE CO., LTD., Futian District (CN)

(72) Inventors: Yinjiong Tan, Shenzhen (CN); Liang Bai, Shenzhen (CN); Chao Yao, Shenzhen (CN); Ruiying Shang, Shenzhen (CN)

(73) Assignee: HONOR DEVICE CO., LTD., Shenzhen (CN)

( * ) Notice: Subject to any disclaimer, the term of this patent is extended or adjusted under 35 U.S.C. 154(b) by 809 days.

(21) Appl. No.: 17/911,345

(22) PCT Filed: Apr. 27, 2022

(86) PCT No.: PCT/CN2022/089639
§ 371 (c)(1),
(2) Date: Sep. 13, 2022

(87) PCT Pub. No.: WO2023/024554
PCT Pub. Date: Mar. 2, 2023

(65) Prior Publication Data
US 2024/0179865 A1 May 30, 2024

(30) Foreign Application Priority Data

Aug. 26, 2021 (CN) ......................... 202122038383.X

(51) Int. Cl.
*H05K 7/14* (2006.01)
*A61B 5/00* (2006.01)
(Continued)

(52) U.S. Cl.
CPC ....... *H05K 7/1427* (2013.01); *A61B 5/02055* (2013.01); *A61B 5/256* (2021.01);
(Continued)

(58) Field of Classification Search
CPC . A61B 5/02055; A61B 5/256; A61B 5/02416; A61B 2562/166;
(Continued)

(56) References Cited

U.S. PATENT DOCUMENTS

| 2014/0275845 A1 | 9/2014 | Eagon et al. |
| 2017/0055882 A1 | 3/2017 | Al-Ali et al. |

(Continued)

FOREIGN PATENT DOCUMENTS

| CN | 106691398 A | 5/2017 |
| CN | 108871609 A | 11/2018 |

(Continued)

*Primary Examiner* — Eric F Winakur
*Assistant Examiner* — Sienna C Pyle
(74) *Attorney, Agent, or Firm* — WOMBLE BOND DICKINSON (US) LLP

(57) ABSTRACT

An electronic device includes a shell, a contact member, a temperature sensor, and a circuit board. The shell has an accommodating space. The contact member is arranged on the shell, and at least part of a surface of the contact member forms an outer surface of the electronic device. The temperature sensor is arranged in the accommodating space and has a positive electrode and a negative electrode. The circuit board is arranged in the accommodating space and provided with a positive wire and a negative wire. The positive wire is connected to the positive electrode of the temperature sensor. The negative wire is connected to the negative electrode of the temperature sensor. At least one of the positive wire and the negative wire is thermally conductively connected to the contact member.

13 Claims, 7 Drawing Sheets

(51) Int. Cl.

| | |
|---|---|
| *A61B 5/0205* | (2006.01) |
| *A61B 5/024* | (2006.01) |
| *A61B 5/256* | (2021.01) |
| *A61B 5/28* | (2021.01) |
| *A61B 5/332* | (2021.01) |
| *G01K 13/20* | (2021.01) |
| *G04G 21/02* | (2010.01) |
| *H05K 1/18* | (2026.01) |
| *H05K 1/181* | (2026.01) |

(52) U.S. Cl.

CPC ................ *A61B 5/28* (2021.01); *A61B 5/681* (2013.01); *G01K 13/20* (2021.01); *H05K 1/181* (2013.01); *A61B 5/02416* (2013.01); *A61B 5/02438* (2013.01); *A61B 5/332* (2021.01); *A61B 2562/166* (2013.01); *G04G 21/025* (2013.01); *H05K 2201/10151* (2013.01)

(58) Field of Classification Search

CPC ............ A61B 2562/0209; A61B 5/681; A61B 5/02438; A61B 5/332; A61B 5/282; A61B 2562/14; H05K 2201/10151; H05K 7/1427

See application file for complete search history.

(56) References Cited

U.S. PATENT DOCUMENTS

| | | | | |
|---|---|---|---|---|
| 2017/0288278 | A1* | 10/2017 | Ming | .................. H01M 10/653 |
| 2017/0296088 | A1 | 10/2017 | Choi | |
| 2019/0208363 | A1* | 7/2019 | Shapiro | ............... A61B 5/0205 |
| 2020/0107877 | A1* | 4/2020 | Koblish | .................. A61B 5/01 |
| 2021/0193977 | A1 | 6/2021 | Reykhert et al. | |
| 2021/0399563 | A1* | 12/2021 | Moon | .................. H02J 7/0044 |
| 2023/0032169 | A1* | 2/2023 | Kim | .................. A61B 5/02438 |

FOREIGN PATENT DOCUMENTS

| | | |
|---|---|---|
| CN | 110584620 A | 12/2019 |
| CN | 210673328 U | 6/2020 |
| CN | 213720299 U | 7/2021 |

* cited by examiner

ELECTRONIC DEVICE

CROSS-REFERENCE TO RELATED APPLICATIONS

This application is a National Stage of International Application No. PCT/CN2022/089639, filed Apr. 27, 2022, which claims priority to Chinese Patent Application No. 202122038383.X, filed Aug. 26, 2021, both of which are hereby incorporated by reference in their entireties.

TECHNICAL FIELD

This application relates to the technical field of electronic devices, and in particular, to an electronic device.

BACKGROUND

As living standards improve, people attach increasing importance to their health statuses. In order to help people learn their health statuses, increasing electronic devices such as watches and bracelets are configured with a health monitoring function, such as temperature measurement. However, accuracy of temperature measurement by current electronic devices is low.

SUMMARY

This application provides an electronic device, to improve measurement accuracy of a temperature sensor, shorten a measurement time of the temperature sensor, and improve sensitivity of the temperature sensor.

To achieve the above purpose, embodiments of this application adopt the following technical solutions:

This application provides an electronic device. The electronic device includes a shell, a contact member, a temperature sensor, and a circuit board. The shell has an accommodating space. The contact member is arranged on the shell, and at least part of a surface of the contact member forms an outer surface of the electronic device. That is to say, a part of the surface of the contact member forms the outer surface of the electronic device, or an entire surface of the contact member forms the outer surface of the electronic device. The temperature sensor is arranged in the accommodating space and has a positive electrode and a negative electrode. The circuit board is arranged in the accommodating space and provided with a positive wire and a negative wire. The positive wire is connected to the positive electrode of the temperature sensor. The negative wire is connected to the negative electrode of the temperature sensor. At least one of the positive wire and the negative wire is thermally conductively connected to the contact member. The temperature sensor is configured to perform temperature measurement according to a temperature transferred from the at least one of the positive wire and the negative wire.

According to the electronic device provided in this application, heat conduction is enabled between at least one of the positive wire and the negative wire of the circuit board and the contact member, so that the temperature sensor can perform temperature measurement according to the temperature transferred from the at least one of the positive wire and the negative wire. In this way: heat conduction efficiency of heat transfer from a human skin to the temperature sensor is improved, a temperature measurement time is shortened, sensitivity of the temperature sensor is enhanced, and a heat loss during the heat conduction is reduced, thereby improving accuracy of temperature measurement.

In a possible implementation, a thermal conductivity k1 of the contact member satisfies: k1≥15 W/m·K. Therefore, heat conduction performance of the contact member can be ensured, so that a temperature of the human skin can be quickly transferred to the contact member, and the temperature in the contact member can be quickly transferred to the temperature sensor for detection. In this way, a temperature transfer time is shortened, thereby shortening a temperature detection time, and improving the detection sensitivity of the temperature sensor.

In a possible implementation, the electronic device further includes an insulating and thermally conductive member, and the at least one of the positive wire and the negative wire is thermally conductively connected to the contact member by the insulating and thermally conductive member. In this way: the temperature in the contact member can be transferred to the positive wire and/or the negative wire through the insulating and thermally conductive member. Compared with a solution in which the contact member is directly connected to the positive wire and/or the negative wire, in the solution of the embodiments of this application, the heat can be transferred more effectively, and heat dissipation can be reduced. In addition, even if the contact member is a conductive member, the contact member can still be prevented from being electrified, thereby ensuring use safety of the electronic device.

In a possible implementation, a thermal conductivity k2 of the insulating and thermally conductive member satisfies: k2≥10 W/m·K. Therefore, the heat conduction performance of the insulating and thermally conductive member can be ensured, so that the temperature in the contact member can be quickly transferred to the temperature sensor for detection.

In a possible implementation, the electronic device further includes a thermal insulator wrapped around at least part of an outer surface of the temperature sensor. The thermal insulator may be wrapped around a part of the outer surface of the temperature sensor, or may be wrapped around an entire outer surface of the temperature sensor. The thermal insulator can separate the temperature sensor from other components on the circuit board, so that heat exchange between the temperature sensor and the outside can be reduced, thereby preventing heat generated by the other components on the circuit board from affecting the temperature sensor. In this way, accuracy of a measurement of the temperature sensor is improved.

In a possible implementation, the contact member and the temperature sensor are arranged on two opposite sides of the circuit board. By arranging the contact member and the temperature sensor on the two opposite sides of the circuit board, a gap between the contact member and the positive wire and/or the negative wire is reduced, thereby facilitating the heat conduction between the contact member and the positive wire and/or the negative wire, reducing assembly difficulty, and realizing a more proper layout of an internal structure of the electronic device. Therefore, the structure of the electronic device is more compact, thereby facilitating lightening and thinning of the electronic device.

In a possible implementation, the circuit board includes a multi-layer wire structure formed by a metal layer and insulating dielectric layers that are alternately arranged in sequence. The positive wire includes a positive wire body and a first metallized via, the positive wire body is formed on the metal layer, the first metallized via extends through surfaces on the two opposite sides of the circuit board, and the positive wire body is electrically connected to the first metallized via. The negative wire includes a negative wire body and a second metallized via the negative wire body is formed on the metal layer, the second metallized via extends through the surfaces on the two opposite sides of the circuit board, and the negative wire body is electrically connected to the second metallized via. At least one of the first metallized via and the second metallized via is thermally conductively connected to the contact member. In this way, the at least one of the positive wire and the negative wire can be thermally conductively connected to the contact member conveniently, and the structure of the electronic device can be simplified.

In a possible implementation, the positive wire further includes a first positive pad and a second positive pad arranged opposite to each other on two ends of the first metallized via, and the first positive pad is electrically connected to the positive electrode of the temperature sensor. The negative wire further includes a first negative pad and a second negative pad arranged opposite to each other on one end of the second metallized via, and the first negative pad is electrically connected to the negative electrode of the temperature sensor. At least one of the second positive pad and the second negative pad is thermally conductively connected to the contact member.

In this way, the at least one of the positive wire and the negative wire can be thermally conductively connected to the contact member conveniently. In addition, by arranging the contact member and the temperature sensor on the two opposite sides of the circuit board, a gap between the contact member and the positive wire and/or the negative wire can be further reduced, thereby facilitating the heat conduction between the contact member and the positive wire and/or the negative wire, reducing assembly difficulty of assembly, and realizing a more proper layout of an internal structure of the electronic device. In this way, the structure of the electronic device is more compact, thereby facilitating lightening and thinning of the electronic device.

In a possible implementation, the electronic device includes a charging electrode and a detection electrode configured to detect vital sign information, the charging electrode and the detection electrode are arranged on the shell, and at least part of a surface of the charging electrode (a part of the surface of the charging electrode or an entire surface of the charging electrode) and at least part of a surface of the detection electrode (a part of the surface of the detection electrode or an entire surface of the detection electrode) form the outer surface of the electronic device. At least one of the charging electrode and the detection electrode forms the contact member. Since the charging electrode or the detection electrode of the electronic device is used as the contact member of the temperature sensor, and the temperature of the human skin is transferred to the temperature sensor through the charging electrode or the detection electrode, the contact member for heat conduction with the temperature sensor is not required to be additionally arranged when the electronic device is provided with the charging electrode or the detection electrode. In this way: a space occupied by the contact member is saved, thereby saving a space occupied in an overall design space of the electronic device. Therefore, more detection devices can be integrated on the electronic device without increasing an area of the cover plate, so that functions of the electronic device are enriched. Moreover, holes required on the shell can be reduced, thereby improving waterproof performance of the electronic device.

In a possible implementation, an impedance Z of the contact member satisfies: $Z \leq 1\Omega$. In this embodiment, by setting the impedance of the contact member to be less than $1\Omega$, when the contact member is the charging electrode or the detection electrode, it is ensured that the temperature of the human skin can be quickly transferred to the temperature sensor, the sensitivity of the temperature sensor and the accuracy of temperature measurement are improved, and signals of excellent quality of the charging electrode or the detection electrode are ensured.

In a possible implementation, the detection electrode is configured to detect an electrocardiogram electrode of an electrocardiogram. In this way, electrocardiogram information of a user can be easily obtained, thereby facilitating monitoring of a health status of the user.

In a possible implementation, the detection electrode includes a first electrode and a second electrode, the first electrode and the second electrode are both arranged on the shell and are spaced apart from each other, at least part of the first electrode and at least part of the second electrode are exposed from the shell, and the part of the first electrode exposed from the shell and the part of the second electrode exposed from the shell define an annular structure. In this way, an area of contact between the first electrode and the second electrode and a human body can be increased. In addition, the annular structure can improve stability of the contact between the detection electrode and the human body, thereby improving accuracy of a detection result of the detection electrode. In addition, when the detection electrode is an ECG electrode, that is, the first electrode and the second electrode are both the ECG electrode, if the first electrode and the second electrode are spaced apart from each other, common mode rejection (common mode rejection. CMR) performance of the ECG electrode can be improved. Therefore, anti-interference performance of the ECG electrode is improved, so that signal quality of the ECG electrode is further improved, and the detection result is more accurate.

In a possible implementation, the charging electrode includes a positive electrode and a negative electrode arranged on an extending path of the annular structure or on an extended line of the extending path. Therefore, a space of the shell can be properly used, so that the overall layout of the electronic device is more proper, and the charging electrode and the detection electrode can be integrated on the shell, so that the functions of the electronic device are more diverse.

In a possible implementation, the electronic device further includes a photoplethysmography detection device, where a detection light window of the photoplethysmography detection device is arranged on an inner side of the annular structure. In this way, the space of the shell can be properly used, so that the overall structure of the electronic device is more compact. Therefore, the detection light window of the photoplethysmography detection device, the ECG electrode, the charging electrode, and the contact member of the temperature sensor can all be integrated on the cover plate of the electronic device without increasing the area of the cover plate, so that the electronic device can simultaneously detect PPG detection data. ECG detection data, and body temperature detection data of a user, thereby obtaining data of the user reflecting a health status, such as a pulse, a heart rate, a blood pressure, and an electrocardiogram. In addition, the electronic device can determine emotion and tension of the user according to the ECG detection data and the body temperature detection data, thereby monitoring the health status of the user more comprehensively.

In a possible implementation, an area of the detection light window is substantially the same as an area of the inner side of the annular structure. In this way, the detection area of the detection light window can be increased, thereby ensuring that light of the PPG detection device is not blocked, and improving detection accuracy of the PPG detection device.

In a possible implementation, the shell includes a cover plate and a side frame surrounding a periphery of the cover plate. A protruding portion protruding away from a center of the accommodating space is arranged on the cover plate, and the contact member is arranged on the protruding portion. Therefore, the contact member can come into contact with a human skin, and an area of contact between the cover plate of the electronic device and a wrist skin can be increased when the electronic device is worn on a wrist, thereby improving comfort of the electronic device.

In a possible implementation, the temperature sensor is a digital temperature sensor. Therefore, the temperature measurement accuracy can be improved, and the space occupied by the temperature sensor can be reduced, thereby facilitating lightening and thinning of the electronic device. In addition, power consumption of electronic device can be reduced.

REFERENCE NUMERALS

Figures 1, 2:
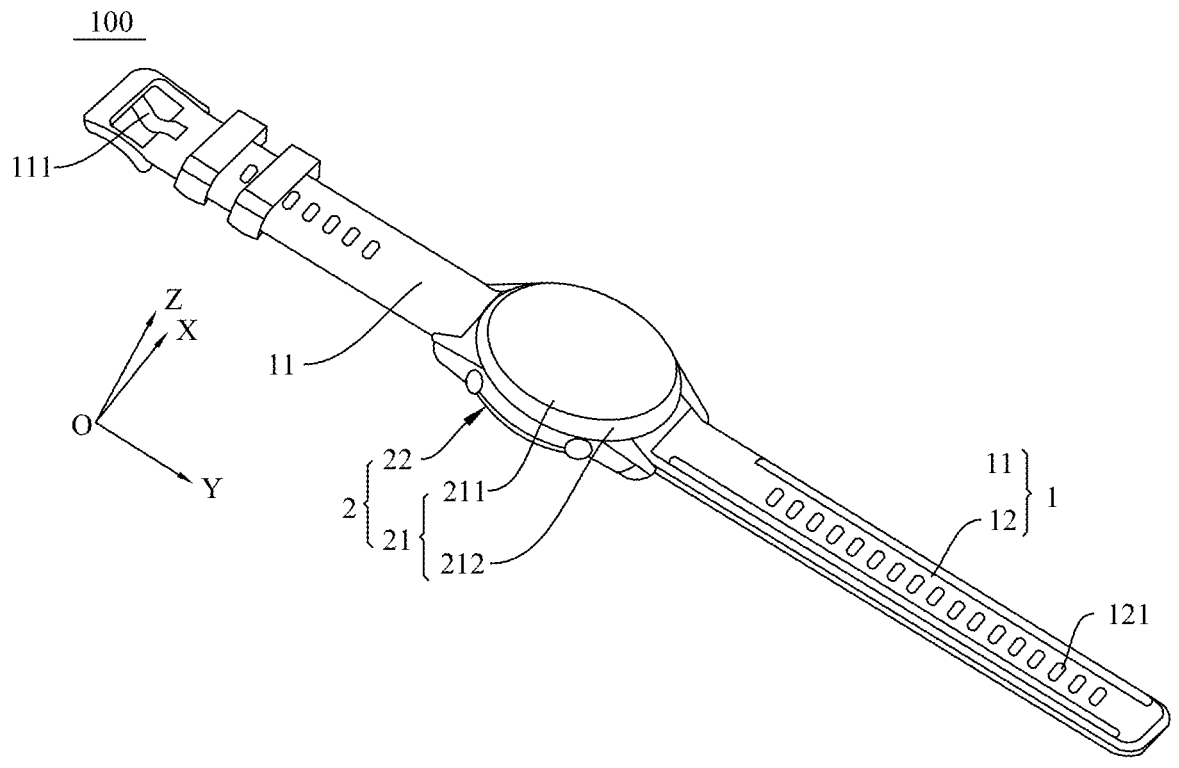
FIG. 1 is a schematic structural diagram of an electronic device according to some embodiments of this application.
FIG. 2 is a schematic diagram of a main body of the electronic device according to an embodiment of this application.

100. Electronic device
1. Watchband; 11: First watchband; 111. First locking portion; 12. Second watchband; 121. Second locking portion;
2. Main body;
21. Display module; 211. Screen; 211a. Light-transmissive cover plate; 211b. Display; 212. Decorative ring;
22. Shell;
22a. Cover plate; 221. First embedding groove; 221a. First communication hole; 222. Second embedding groove; 222a. Second communication hole; 223. Protruding portion; 224. First via; 225. Second via; 226. First spacer region; 227. Second spacer region; 228. Detection light window;
22b. Side frame;
3. Circuit board; 31. Metal layer; 31a. First metal layer; 31b. Second metal layer; 31c. Intermediate metal layer; 32. Insulating dielectric layer; 33. First solder mask layer; 33a. First hollowed-out portion; 34. Second solder mask layer; 34a. Second hollowed-out portion; 35. Positive wire; 35a. Positive wire body; 35b. First metallized via; 35c. First positive pad; 35d. Second positive pad; 36. Negative wire; 36a. Negative wire body; 36b. Second metallized via; 36c. First negative pad; 36d. Second negative pad;
301. Processor;
4. Temperature sensor; 4a. Positive electrode; 4b. Negative electrode; 401. Positive welding leg; 402. Negative welding leg; 41. Insulating housing; 42. Temperature sensing element;
5. Insulating and thermally conductive member;
6. Thermal insulator;
7. Detection electrode; 71. First electrode; 711. First body portion; 712. First protruding portion; 71a. First end; 71b. Second end; 71c. First avoidance hole; 72. Second electrode; 721. Second body portion; 722. Second protruding portion; 72a. Third end; 72b. Fourth end; 72c. Second avoidance hole; 73. ECG electrode;
8. Charging electrode; 81. Positive electrode; 82. Negative electrode;
91. Light-emitting element; 92. Light detector;
200. Skin tissue; 300. Artery; 400. Muscle tissue.

DESCRIPTION OF EMBODIMENTS

In the embodiments of this application, terms "first", "second", "third", and "fourth" are used merely for the purpose of description, and shall not be construed as indicating or implying relative importance or implying a quantity of indicated technical features. Therefore, features defining "first", "second", "third", and "fourth" may explicitly or implicitly include one or more such features.

In the embodiments of this application, the terms "include", "comprise", and any variants thereof are intended to cover a non-exclusive inclusion. Therefore, in the context of a process, method, object, or apparatus that includes a series of elements, the process, method, object, or apparatus not only includes such elements, but also includes other elements not specified expressly, or may include inherent elements of the process, method, object, or apparatus. Without more limitations, elements defined by the sentence "including one" does not exclude that there are still other same elements in the processes, methods, objects, or apparatuses.

"And/or" in the embodiments of this application describes only an association relationship for describing associated objects and represents that three relationships may exist. For example, A and/or B may represent the following three cases: Only A exists, both A and B exist, and only B exists. In addition, the character "/" in this specification generally indicates an "or" relationship between the associated objects.

This application provides an electronic device 100. The electronic device 100 can detect a temperature of a human body to determine a health status of the human body. Specifically, in the electronic device 100 provided in this application, a temperature sensor 4 configured to detect the temperature of the human body is arranged, and a positive wire and a negative wire of the temperature sensor 4 are in contact with a contact member on a shell 22, so as to transfer the temperature of the human body to the temperature sensor 4 through the contact member, the positive wire, and the negative wire in sequence for measurement, thereby ensuring accuracy and sensitivity of the temperature detection.

Specifically; the electronic device 100 includes, but is not limited to a wearable device (for example, a watch, a wristband, and smartglasses), a phone, a tablet personal computer (tablet personal computer), a laptop computer (laptop computer), a personal digital assistant (personal digital assistant, PDA), a personal computer, a notebook (notebook), an in-vehicle device, and other electronic devices 100.

Referring to FIG. 1, FIG. 1 is a schematic structural diagram of an electronic device 100 according to some embodiments of this application. In this embodiment, the electronic device 100) is a watch or a bracelet. For ease of description, the following embodiments are all described by using an example that the electronic device 100 is a watch, but this should not be construed as a limitation on this application.

It may be understood that FIG. 1 and the following related drawings only schematically show some components included in the electronic device 100, and actual shapes, actual sizes, actual positions, and actual structures of the components are not defined by FIG. 1 and the following drawings.

In order to facilitate the description of the following embodiments, an XYZ coordinate system is established. Specifically, a width direction of the electronic device 100 is defined as an X-axis direction, a length direction of the electronic device 100 is defined as a Y-axis direction, and a thickness direction of the electronic device 100 is defined as a Z-axis direction. It may be understood that the coordinate system of the electronic device 100 may be flexibly set according to actual requirements. This is not specifically limited herein.

Specifically, referring to FIG. 1, the electronic device 100 includes a main body 2 and a watchband 1. The watchband 1 may include a first watchband 11 and a second watchband 12. The first watchband 11 and the second watchband 12 may be arranged on two opposite sides of the main body 2 along the Y-axis direction. A first locking portion 111 is arranged on the first watchband 11, and a second locking portion 121 is arranged on the second watchband 12. The first locking portion 111 and the second locking portion 121 are detachably locked to each other, so that the electronic device 100 can be worn on a wrist of a user. It should be understood that the mating structure of the first locking portion 111 and the second locking portion 121 may be a buckle structure such as a hook buckle, a concealed buckle, a butterfly buckle, a belt buckle, a foldable safety buckle, a foldable buckle, or a pin buckle. This is not specifically limited in this application.

Figure 3A:
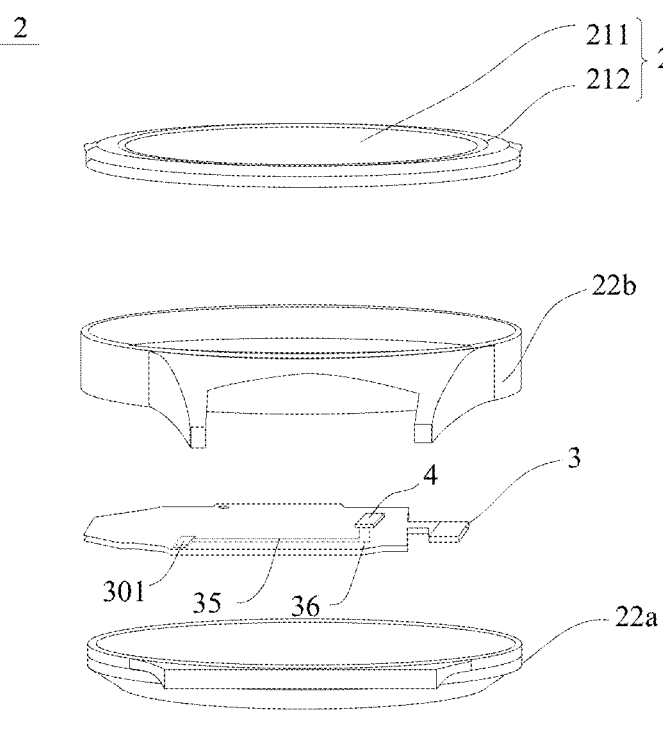
FIG. 3a is an exploded view of the main body of the electronic device according to an embodiment of this application.

Referring to FIG. 2 and FIG. 3a, FIG. 2 is a perspective view of the main body 2 of the electronic device 100 according to an embodiment of this application, and FIG. 3a is an exploded view of the main body 2 of the electronic device 100 according to an embodiment of this application. The main body 2 may include a display module 21, a shell 22, a circuit board 3, a battery, and a temperature sensor 4. In some other embodiments, the electronic device 100 may not include the display module 21.

Figure 3B:
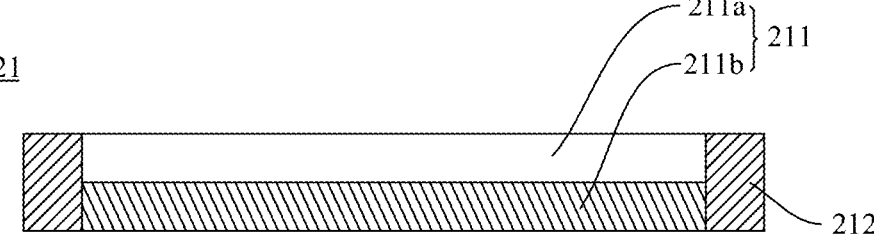
FIG. 3b is a cross-sectional view of a screen of the electronic device according to some embodiments of this application.

Referring to FIG. 3b, the display module 21 includes a screen 211 and a decorative ring 212. The decorative ring 212 surrounds a periphery of the screen 211. The decorative ring 212 can protect and decorate the periphery of the screen 211. The screen 211 includes a light-transmissive cover plate 211a and a display 211b. The light-transmissive cover plate 211a and the display 211b are stacked and fixedly connected. The light-transmissive cover plate 211a is mainly configured to protect and prevent dust for the display 211b. A material of the light-transmissive cover plate 211a includes but is not limited to glass.

The display 211b is configured to display images, videos, data, and the like. The display 211b may be a flexible display or a rigid display. For example, the display 211b may be an organic light-emitting diode (organic light-emitting diode. OLED) display, an active-matrix organic light-emitting diode (active-matrix organic light-emitting diode. AMO-LED) display, a mini light-emitting diode (mini organic light-emitting diode) display, a micro light-emitting diode (micro organic light-emitting diode) display, a micro organic light-emitting diode (micro organic light-emitting diode) display, a quantum dot light-emitting diode (quantum dot light emitting diodes. QLED) display, or a liquid crystal display (liquid crystal display. LCD).

It should be noted that a shape of the screen 211 is not limited in this application. A display surface of the screen 211 may be circular or rectangular. When the shape of the screen 211 changes, shapes of other components such as the shell 22 and the decorative ring 212 of the main body 2 change with the shape of the screen 211. For ease of description, the following descriptions are made by using an example that the display surface of the screen 211 is circular.

The shell 22 has an accommodating space therein. The shell 22 is configured to accommodate and protect the internal electronic components of the electronic device 100. Referring to FIG. 2, the shell 22 may include a cover plate 22a and a side frame 22b, and the side frame 22b surrounds a periphery of the cover plate 22a. The cover plate 22a and the display 211b are stacked. The side frame 22b is arranged between a back cover and the display 211b, and the side frame 22b is fixed to the cover plate 22a. Exemplarily, the side frame 22b may be fixedly connected to the cover plate 22a by an adhesive. The side frame 22b may alternatively be integrally formed with the cover plate 22a, that is, the side frame 22b and the cover plate 22a are an integral structure. The decorative ring 212 of the display module 21 is fixed to the side frame 22b. In some embodiments, the decorative ring 212 may be fixed to the side frame 22b by an adhesive. The above accommodating space in the shell 22 may be defined by the screen 211, the cover plate 22a, and the side frame 22b. The accommodating space accommodates the circuit board 3, the temperature sensor 4, the battery, and the like.

Figure 4:
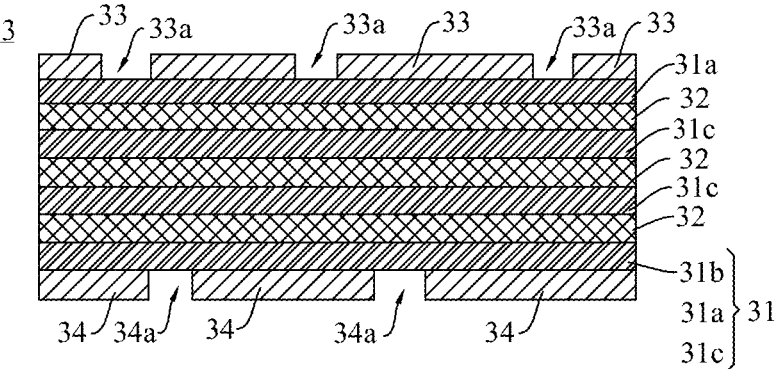
FIG. 4 is a cross-sectional view of a circuit board of the electronic device according to some embodiments of this application.

The circuit board 3 is a carrier configured to realize electrical connection of the electronic components. FIG. 4 is a cross-sectional view of the circuit board 3 of the electronic device 100 according to some embodiments of this application. Referring to FIG. 4, the circuit board 3 includes a multi-layer wire structure formed by a metal layer 31 and insulating dielectric layers 32 that are alternately arranged in sequence. The multi-layer wire structure has a first surface and a second surface. The metal layer 31 of the multilayer wire structure includes a first metal layer 31a and a second metal layer 31b. The first metal layer 31a forms the first surface, and the second metal layer 31b forms the second surface. A first solder mask layer 33 is arranged on the first surface of the multi-layer wire structure, and a second solder mask layer 34 is arranged on the second surface of the multi-layer wire structure. The first solder mask layer 33 and the second solder mask layer 34 may be green ink, black ink, or the like. In a subsequent soldering process, the first solder mask layer 33 and the second solder mask layer 34 can prevent solder from being deposited on a surface of the circuit board 3.

Further, the metal layer 31 of the multi-layer wire structure may further include at least one intermediate metal layer 31c. The intermediate metal layer 31c is arranged between the first metal layer 31a and the second metal layer 31b. Signal lines may be arranged on the first metal layer 331a, the second metal layer 31b, and the intermediate metal layer 31c. The signal lines may include a positive wire 35 and a negative wire 36. In the circuit board 3, the signal lines in the different metal layers 31 are connected through metallized vias.

In some embodiments, the first metal layer 31a, the second metal layer 31b, and the intermediate metal layer 31c may be copper foil layers. The wires on the first metal layer 31a, the second metal layer 31b, and the intermediate metal layer 31c may be formed by a lithography-and-etching process.

Specifically; the first solder mask layer 33 has first hollowed-out portions 33a, and the second solder mask layer 34 has second hollowed-out portions 34a. A part of the signal line on the first metal layer 31a may be exposed from the first hollowed-out portions 33a, so that components can be electrically connected to the signal line on the first metal layer 31a. A part of the signal line on the second metal layer 31b may be exposed from the second hollowed-out portions 34a, so that components can be electrically connected to the signal line on the second metal layer 31b.

It may be understood that the circuit board 3 may be a rigid printed circuit, a flexible printed circuit, or a flexible-rigid printed circuit. The circuit board 3 may be an FR-4 dielectric board, a Rogers (Rogers) dielectric board, an FR-4 and Rogers mixed dielectric board, or the like. FR-4 herein is a mark of a flame-resistant material grade, and the Rogers dielectric board is a high-frequency board.

A processor 301 may be arranged on the circuit board 3. The display 211 and the temperature sensor 4 are both electrically connected to the processor 301. In this way, the temperature detected by the temperature sensor 4 can be displayed on the display 211b after being processed by the processor.

The battery is arranged in the accommodating space. The battery is configured to supply power to the electronic components such as the display 211b and the circuit board 3 in the electronic device 100. In some embodiments, a battery mounting slot is provided in the shell 22, and the battery is mounted in the battery mounting slot.

Figure 4A:
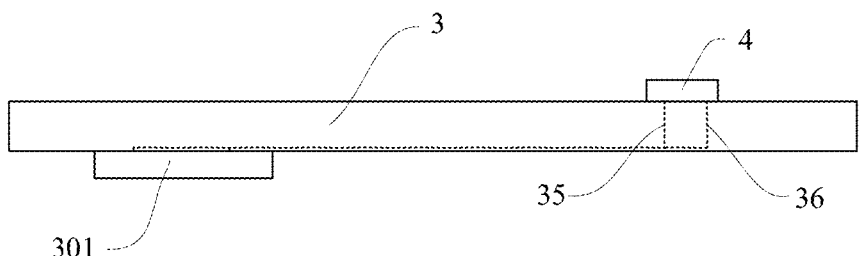
FIG. 4a is a schematic diagram of the circuit board of the electronic device according to some embodiments of this application.
Figure 4B:
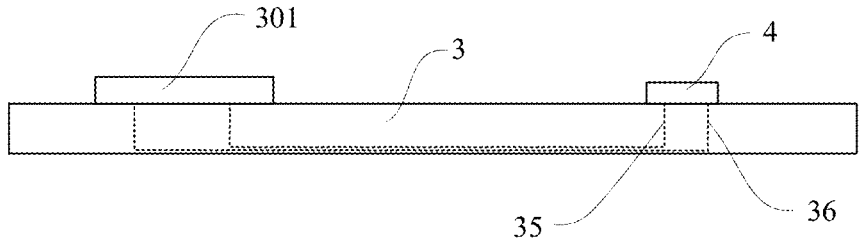
FIG. 4b is a schematic diagram of a circuit board of an electronic device according to some other embodiments of this application.

Specifically, referring to FIG. 4a and FIG. 4b, the temperature sensor 4 has a positive electrode 4a and a negative electrode 4b. The positive electrode 4a of the temperature sensor 4 is connected to the positive wire 35 of the circuit board 3, the negative electrode 4b of the temperature sensor 4 is connected to the negative wire 36 of the circuit board 3, and the processor 301 is electrically connected to the positive wire 35 and the negative wire 36, so that electrical connection between the temperature sensor 4 and the processor 301 can be realized.

In some embodiments, referring to FIG. 4a, the temperature sensor 4 and the processor 301 may be arranged on a same side surface of the circuit board 3. In some other embodiments, referring to FIG. 4b, the temperature sensor 4 and the processor 301 may be arranged on two opposite side surfaces of the circuit board 3 respectively.

In some embodiments, a contact member is arranged on the shell 22, and heat can be conducted between the temperature sensor 4 and the contact member. At least part of the surface of the contact member forms an outer surface of the electronic device 100. That is to say, at least part of the surface of the contact member is exposed from the shell 22. The part of the surface of the contact member forming the outer surface of the electronic device 100 may come into contact with the human skin, and the part of the surface may be formed as a contact surface. In some embodiments, an area of the contact surface may be greater than or equal to 20 square millimeters, and the contact surface may be a flat surface or an arcuate surface, which may be specifically designed according to a physiological structure of a human body. In this way, the contact surface can come into contact with a user more effectively, thereby facilitating heat conduction.

Therefore, when the human skin comes into contact with the contact member, the contact member can absorb a temperature of the human skin and transfer the temperature of the human skin to the temperature sensor 4, so that the temperature of the human body can be detected by the temperature sensor 4. In this way, a health status of the user can be conveniently monitored through the electronic device 100. Therefore, by arranging the contact member on the shell 22 and thermally conductively connecting the contact member to the temperature sensor 4, the temperature of the human body can be conveniently detected while the temperature sensor 4 is arranged in in the shell 22, thereby improving reliability of the temperature sensor 4.

Figure 5:
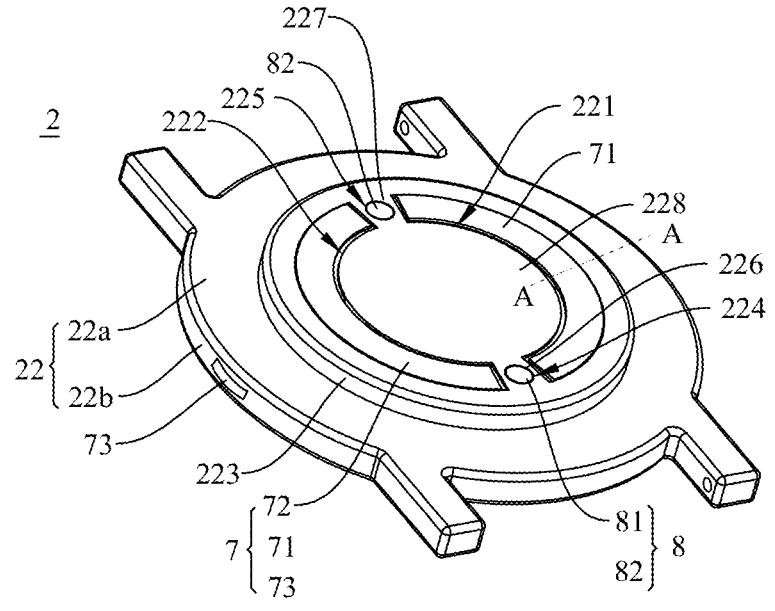
FIG. 5 is a schematic structural diagram of a main body of an electronic device according to some other embodiments of this application.
Figure 6:
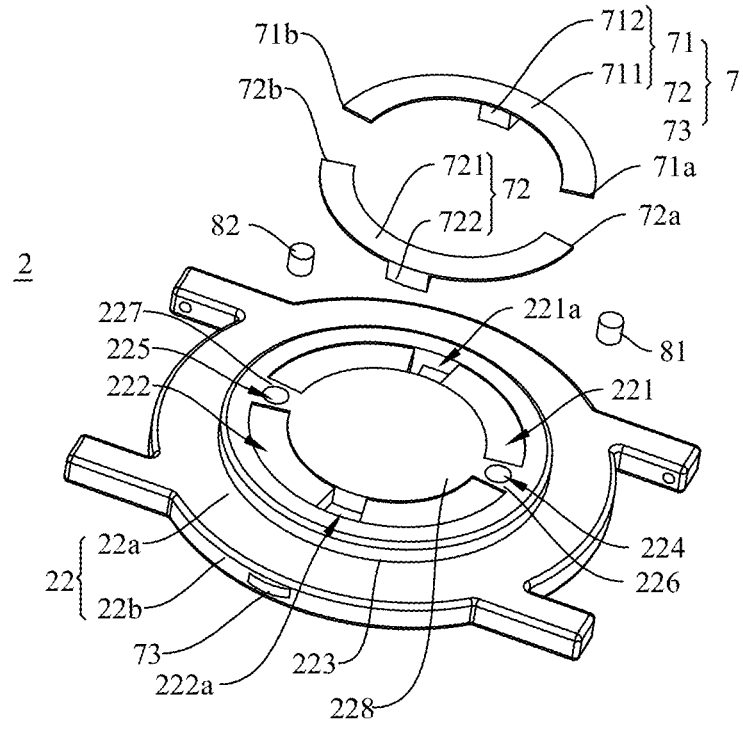
FIG. 6 is an exploded view of the main body of the electronic device shown in FIG. 5.

It may be understood that, the contact member may be arranged on a cover plate 22a of the shell 22 or on a side frame 22b of the shell 22. Referring to FIG. 5 and FIG. 6, FIG. 5 is a schematic structural diagram of a main body 2 of an electronic device 100 according to some other embodiments of this application, and FIG. 6 is an exploded view of the main body 2 of the electronic device 100 shown in FIG. 5. In this embodiment, the contact member is arranged on the cover plate 22a. An outer surface of the contact member and an outer surface of the cover plate 22a may be arranged on a same surface, or the outer surface of the contact member may protrude outward from the outer surface of the cover plate 22a. In this way, the contact member can conveniently come into contact with the human skin.

In some embodiments, referring to FIG. 5 and FIG. 6, a protruding portion 223 that protrudes away from a center of the accommodating space is arranged on the cover plate 22a, and the contact member is arranged on the protruding portion 223. In this embodiment, the outer surface of the contact member and the outer surface of the protruding portion 223 may be arranged on a same plane. Therefore, the contact member can come into contact with a human skin, and an area of contact between the cover plate 22a of the electronic device 100 and a wrist skin can be increased when the electronic device 100 is worn on a wrist, thereby improving comfort of the electronic device 100.

Figure 7:
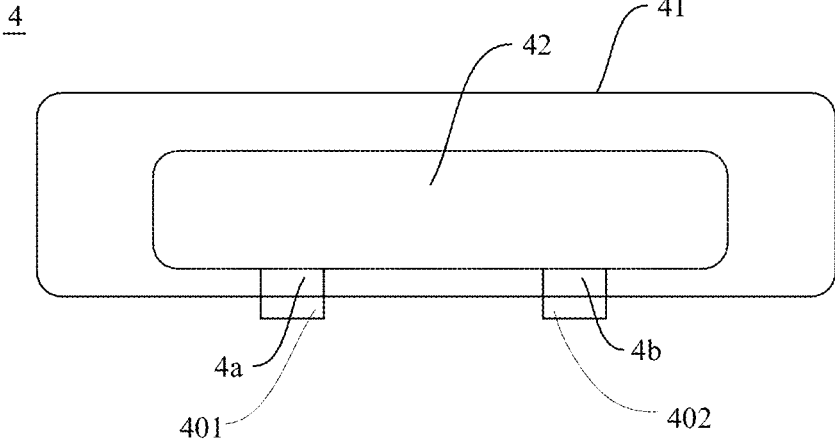
FIG. 7 is a schematic structural diagram of a temperature sensor according to some other embodiments of this application.

FIG. 7 is a schematic diagram of the temperature sensor 4 according to some embodiments of this application. Referring to FIG. 7, in order to improve reliability of the temperature sensor 4, a temperature sensing element 42 of the temperature sensor 4 is usually packaged in an insulating housing 41, and the positive electrode 4a and the negative electrode 4b of the temperature sensor 4 are exposed from the insulating housing 41. Electrical connection between the temperature sensing element 42 and the circuit board 3 is realized by the positive electrode 4a and the negative electrode 4b of the temperature sensor 4. Therefore, during temperature measurement, after the contact member absorbs the temperature of the human skin, the temperature of the human skin is first transferred to the insulating housing 41 of the temperature sensor 4, and then is transferred to the temperature sensing element 42 through the insulating housing 41. Since heat conduction performance of the insulating housing 41 is relatively poor, a heat loss during heat conduction and a temperature transfer time are increased, thus reducing accuracy and sensitivity of the temperature measurement.

Figure 8:
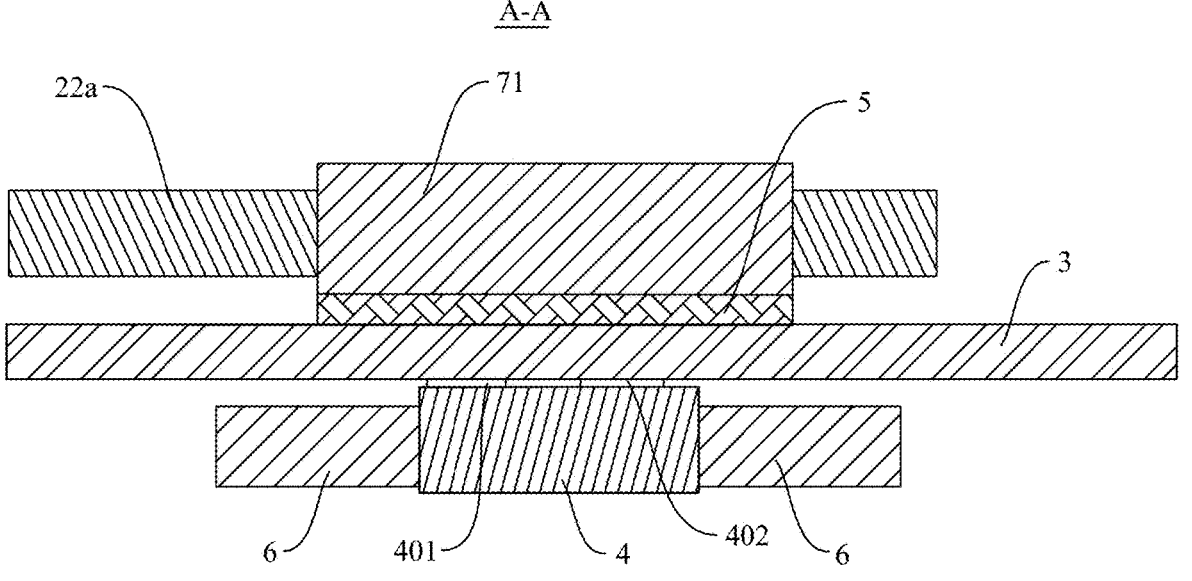
FIG. 8 is a cross-sectional view along a line A-A in FIG. 5.

In order to resolve the above technical problems, refer to FIG. 8, and FIG. 8 is a cross-sectional view along a line A-A in FIG. 5. In the electronic device 100 in this embodiment, heat can be conducted between at least one of the positive wire 35 and the negative wire 36 of the circuit board 3 and the contact member, and the temperature sensor 4 is configured to perform temperature measurement according to the temperature transferred from the at least one of the positive wire 35 and the negative wire 36.

Specifically, heat can be conducted only between the positive wire 35 of the circuit board 3 and the contact member. In this case, the temperature sensor 4 may perform temperature measurement according to the temperature transferred by the positive wire 35. Alternatively, heat can be conducted only between the negative wire 36 of the circuit board 3 and the contact member. In this case, the temperature sensor 4 may perform temperature measurement according to the temperature transferred by the negative wire 36. Alternatively, heat can be conducted between the positive wire 35 of the circuit board 3 and the contact member and between the negative wire 36 of the circuit board 3 and the contact member. In this case, the temperature sensor 4 may perform temperature measurement according to the temperatures transferred by the positive wire 35 and the negative wire 36.

When heat can be conducted between the positive wire 35 of the circuit board 3 and the contact member, since the positive electrode 4a of the temperature sensor 4 is connected to the positive wire 35, the temperature of the contact member can be transferred to the positive electrode 4a of the temperature sensor 4 through the positive wire 35. In this way, the temperature sensor 4 can perform temperature measurement according to the temperature transferred to the positive electrode 4a of the temperature sensor 4. A heat conduction path between the contact member and the temperature sensor 4 is: contact member→positive wire 35→positive electrode 4a of temperature sensor 4→temperature sensing element 42 of temperature sensor 4.

When heat can be conducted between the negative wire 36 of the circuit board 3 and the contact member, since the negative electrode 4b of the temperature sensor 4 is connected to the negative wire 36, the temperature of the contact member can be transferred to the negative electrode 4b of the temperature sensor 4 through the negative wire 36. In this way, the temperature sensor 4 can perform temperature measurement according to the temperature transferred to the negative electrode 4b of the temperature sensor 4. A heat conduction path between the contact member and the temperature sensor 4 is: contact member→negative wire 36→negative electrode 4b of temperature sensor 4→temperature sensing element 42 of temperature sensor 4.

In this way, the human skin heat absorbed by the contact member can be transferred to the temperature sensing element 42 of the temperature sensor 4 through the at least one of the positive wire 35 and the negative wire 36. Since the positive wire 35, the negative wire 36, the positive electrode 4a of the temperature sensor 4, and the negative electrode 4b of the temperature sensor 4 are all made of conductive materials, heat conduction performance thereof is more desirable than that of the insulating housing 41. Therefore, by enabling heat conduction between the at least one of the positive wire 35 and the negative wire 36 of the circuit board 3 and the contact member, heat conduction efficiency of the heat transfer from the human skin to the temperature sensor 4 is improved, the temperature transfer time is shortened, the sensitivity of the temperature sensor 4 is enhanced, and the heat loss during the heat conduction is reduced, thereby improving the accuracy of the temperature measurement.

According to the electronic device 100 provided in this embodiment, heat conduction is enabled between at least one of the positive wire 35 and the negative wire 36 of the circuit board 3 and the contact member, so that the temperature sensor 4 can perform temperature measurement according to the temperature transferred from the at least one of the positive wire 35 and the negative wire 36. In this way, the heat conduction efficiency of the heat transfer from the human skin to the temperature sensor 4 is improved, the temperature measurement time is shortened, the sensitivity of the temperature sensor 4 is enhanced, and the heat loss during the heat conduction is reduced, thereby improving the accuracy of the temperature measurement.

In some embodiments, the temperature sensor 4 is a digital temperature sensor. For example, the temperature sensor 4 may be a CMOS digital temperature sensor. The digital temperature sensor is an ultra-small, ultra-precise, low-power, and low-voltage temperature sensor that does not require user calibration. By using the digital temperature sensor as the temperature sensor 4, the accuracy of the temperature measurement can be improved, and a space occupied by the temperature sensor 4 can be reduced, thereby facilitating lightening and thinning of the electronic device 100. In addition, power consumption of electronic device 100 can be reduced.

In some embodiments, a thermal conductivity $k1$ of the contact member satisfies: $k1 \geq 15$ W/m·K. For example, the contact member may be a stainless steel member obtained by machining a stainless steel material. Optionally, the contact member is a type 316 stainless steel member with a thermal conductivity of 16.2 W/m·K. Certainly, this application is not limited thereto. Therefore, heat conduction performance of the contact member can be ensured, so that the temperature of the human skin can be quickly transferred to the contact member, and the temperature in the contact member can be quickly transferred to the temperature sensor 4 for detection. In this way, the temperature transfer time is shortened, thereby shortening a temperature detection time, and improving the detection sensitivity of the temperature sensor 4.

In some embodiments, referring to FIG. 8, the electronic device 100 further includes a thermal insulator 6, and the thermal insulator 6 is wrapped around at least part of the outer surface of the temperature sensor 4. That is to say, the thermal insulator 6 may be wrapped around a part of the outer surface of the temperature sensor 4, or may be wrapped around an entire outer surface of the temperature sensor 4. The thermal insulator 6 can separate the temperature sensor 4 from other components in the shell 22, so that heat exchange between the temperature sensor 4 and the outside can be reduced, thereby preventing heat generated by the other components in the shell 22 from affecting the temperature sensor 4. In this way, accuracy of a measurement of the temperature sensor 4 is improved.

In some embodiments, the thermal insulator 6 may be rock wool, fiberglass wool, foam, or the like. The thermal insulator 6 may be bonded to the outer surface of the temperature sensor 4. In some other embodiments, the thermal insulator 6 may be a thermally insulating paint, and the thermal insulating paint may be coated on the outer surface of the temperature sensor 4. It may be understood that the material of the thermal insulator 6 is not specifically limited in this application, as long as the thermal insulator 6 can insulate heat.

Figure 9A:
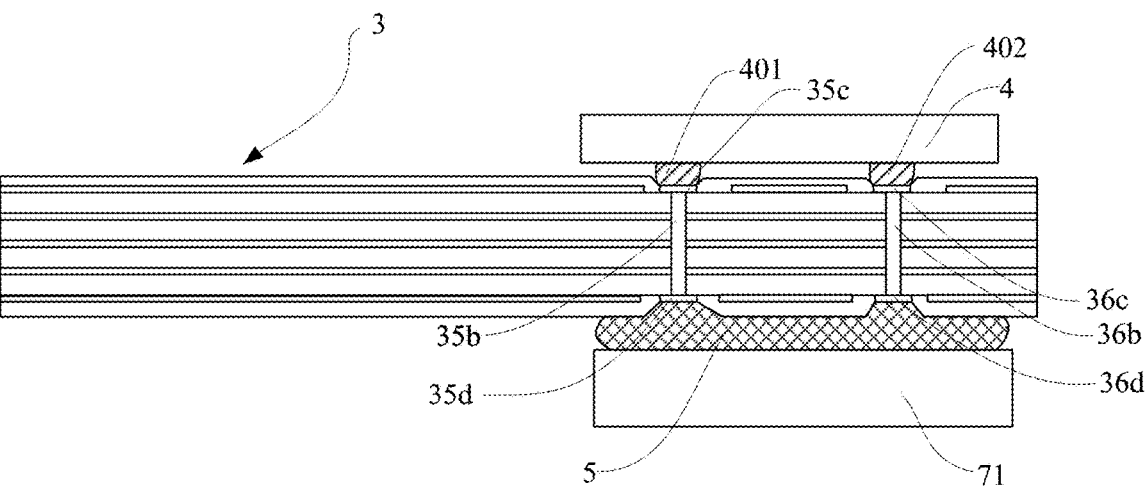
FIG. 9a is a schematic diagram of connection between a temperature sensor and a circuit board according to some embodiments of this application.
Figure 9B:
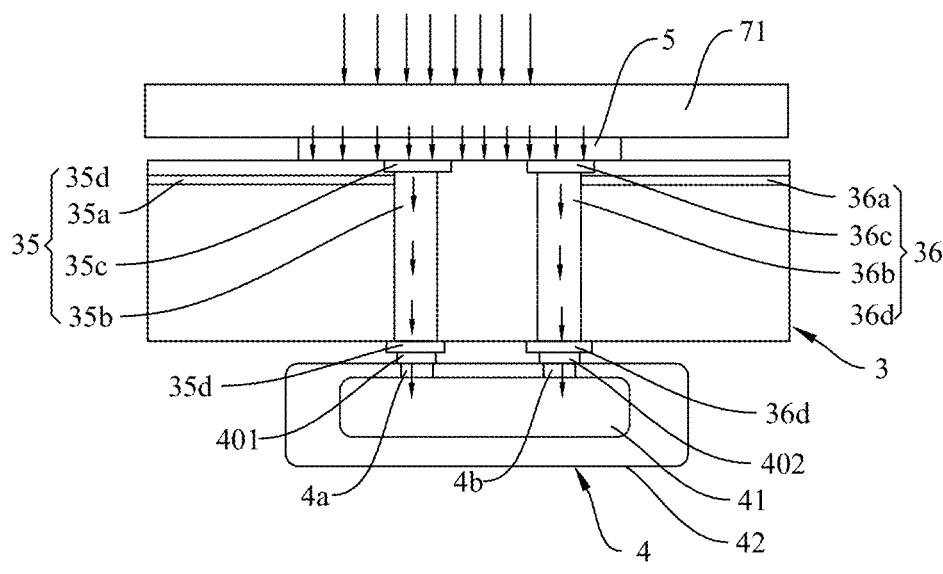
FIG. 9b is a schematic diagram of a temperature transfer path during temperature measurement by the temperature sensor according to some embodiments of this application.

In some embodiments, the positive electrode 4a and the negative electrode 4b of the temperature sensor 4 are connected to the circuit board 3 by pads. FIG. 9a is a schematic diagram of connection between the temperature sensor 4 and the circuit board 3 according to some embodiments of this application, and FIG. 9b is a schematic diagram of a temperature transfer path during temperature measurement by the temperature sensor according to some embodiments of this application. Arrows in FIG. 9b indicate a temperature transfer direction. Referring to FIG. 9a and FIG. 9b, a positive welding leg 401 is arranged on the positive electrode 4a of the temperature sensor 4, and a negative welding leg 402 is arranged on the negative electrode 4b of the temperature sensor 4. The positive wire 35 includes a positive wire body 35a, a first metallized via 35b, and a first positive pad 35c. The positive wire body 35a is formed on the metal layer 31. The first metallized via 35b is provided in the circuit board 3. The first metallized via 35b extends through the two opposite side surfaces of the circuit board 3. The positive wire body 35a is electrically connected to the first metallized via 35b, and the first positive pad 35c is arranged on an end of the first metallized via 35b. The positive welding leg 401 of the temperature sensor 4 is electrically connected to the first positive pad 36c to realize electrical connection between the temperature sensor 4 and the positive wire 35.

The negative wire 36 includes a negative wire body 36a, a second metallized via 36b, and a first negative pad 36c. The negative wire 36a is formed on the metal layer 31, and the second metallized via 36b is provided in the circuit board 3 and extends through the circuit board 3 along a thickness direction of the circuit board 3. The negative wire body 36a is electrically connected to the second metallized via 36b. The first negative pad 36c is arranged on an end of the second metallized via 36b. The first negative pad 36c forms the outer surface of the circuit board 3. The negative welding leg 402 of the temperature sensor 4 is electrically connected to the first negative pad 36c to realize electrical connection between the temperature sensor 4 and the negative wire 36. In this way, the electrical connection between the temperature sensor 4 and the positive wire 35 and the negative wire 36 of the circuit board 3 can be easily realized.

In this embodiment, the human skin heat absorbed by the contact member can be transferred to the positive electrode 4a of the temperature sensor 4 and/or the negative electrode 4b of the temperature sensor 4 through at least one of the first positive pad 35c and the first negative pad 36c, and then is transferred to the temperature sensing element 42 of the temperature sensor 4. In this way, the electrical connection between the temperature sensor 4 and the circuit board 3 can be easily realized, assembly difficulty is reduced, and the sensitivity of the temperature sensor 4 and the accuracy of the temperature measurement can be ensured.

In some other embodiments, the positive wire 35 may not include the first positive pad 35c. In this embodiment, the positive welding leg 401 of the temperature sensor 4 may be electrically connected to the first metallized via 35b to realize the electrical connection between the temperature sensor 4 and the positive wire 35. The negative wire 36 may not include the first negative pad 36c. In this embodiment, the negative welding leg 402 of the temperature sensor 4 may be electrically connected to the second metallized via 36b to realize the electrical connection between the temperature sensor 4 and the negative wire 36. In this way, the electrical connection between the temperature sensor 4 and the positive wire 35 and the negative wire 36 can also be realized, and the structure of the electronic device 100 can be simplified.

Further, the contact member and temperature sensor 4 are arranged on the two opposite sides of the circuit board 3. Referring to FIG. 9a and FIG. 9b, the temperature sensor 4 is arranged on a side of the circuit board 3 facing away from the contact member.

Referring to FIG. 9a and FIG. 9b, the positive wire 35 further includes a second positive pad 35d, and the negative wire 36 further includes a second negative pad 36d. The second positive pad 35d and the second negative pad 36d are arranged on a side surface of the circuit board 3 facing away from the temperature sensor 4, the second positive pad 35d and the first positive pad 35c are arranged on two ends of the first metallized via 35b opposite to each other, and the second negative pad 36d and the first negative pad 36c are arranged on two ends of the second metallized via 36b opposite to each other. The contact member may be thermally conductively connected to the second positive pad 35d to realize heat conduction between the contact member and the positive wire 35, and/or the contact member may be thermally conductively connected to the second negative pad 36d to realize heat conduction between the contact member and the negative wire 36. In this way, the temperature in the contact member can be transferred to the temperature sensing element 42 of the temperature sensor 4.

In this way, thermally conductive connection between the at least one of the positive wire 35 and the negative wire 36 and the contact member can be realized. In addition, by arranging the contact member and the temperature sensor 4 on the two opposite sides of the circuit board 3, a gap between the contact member and the positive wire 35 and/or the negative wire 36 can be further reduced, thereby facilitating the heat conduction between the contact member and the positive wire 35 and/or the negative wire 36, reducing assembly difficulty, and realizing a more proper layout of an internal structure of the electronic device 100. Therefore, the structure of the electronic device 100 is more compact, thereby facilitating lightening and thinning of the electronic device 100.

It may be understood that, in some other embodiments, the positive wire 35 may not include the second positive pad 35d, and the negative wire may not include the second negative pad 36d. In this embodiment, the contact member may be directly thermally conductively connected to at least one of the first metallized via 35b and the second metallized via 36b, so as to realize the heat conduction between the contact member and the positive wire 35 and/or the negative wire 36. In this way, the temperature in the contact member can be transferred to the temperature sensing element 42 of the temperature sensor 4. In this way, the heat conduction between the contact member and the positive wire 35 and/or the negative wire 36 can be realized, and the structure of the electronic device 100 can be simplified.

In some embodiments, the electronic device 100 further includes an insulating and thermally conductive member 5, and at least one of the positive wire 35 and the negative wire 36 is thermally conductively connected to the contact member by the insulating and thermally conductive member 5. Referring to FIG. 8 and FIG. 9a, the insulating and thermally conductive member 5 may cover a side surface of the contact member close to the circuit board 3. A thermal conductivity k2 of the insulating and thermally conductive member 5 satisfies: k2≥10 W/m·K. For example, the insulating and thermally conductive member 5 may be thermally conductive silicone, thermally conductive silicone grease, thermally conductive adhesive, or the like.

Specifically, when heat conduction is enabled between the positive wire 35 and the contact member, the insulating and thermally conductive member 5 may be arranged between the positive wire 35 and the contact member. When heat conduction is enabled between the negative wire 36 and the contact member, the insulating and thermally conductive member 5 may be arranged between the negative wire 36 and the contact member. For example, in an example in FIG. 9a, the insulating and thermally conductive member 5 may cover the second positive pad 35d and the second negative pad 36d. In this way, the temperature in the contact member can be transferred to the positive wire 35 and/or the negative wire 36 through the insulating and thermally conductive member 5. Compared with a solution in which the contact member is directly connected to the positive wire 35 and/or the negative wire 36, in the solution of the embodiments of this application, the heat can be transferred more effectively, and heat dissipation can be reduced. In addition, even if the contact member is a conductive member, the contact member can still be prevented from being electrified, thereby ensuring use safety of the electronic device 100.

In some embodiments of this application, the electronic device includes a charging electrode 8 and a detection electrode 7 configured to detect vital sign information. The charging electrode 8 and the detection electrode 7 are arranged on the shell 22. At least part of a surface of the charging electrode 8 and at least part of a surface of the detection electrode 7 form the outer surface of the electronic device 100, and at least one of the charging electrode 8 and the detection electrode 7 forms the contact member. That is to say, the charging electrode 8 forms the contact member, the detection electrode 7 forms the contact member, or both the charging electrode 8 and the detection electrode 7 form the contact member.

The charging electrode 8 may be electrically connected to the battery of the electronic device 100, so that when the charging electrode 8 is connected to an external power supply, the battery can be charged by the charging electrode 8. In some embodiments, referring to FIG. 5 and FIG. 6, the charging electrode 8 includes a positive electrode 81 and a negative electrode 82. The positive electrode 81 and the negative electrode 82 both may be formed as a cylindrical structure, but this application is not limited thereto.

Specifically, referring to FIG. 6, a first via 224 and a second via 225 are arranged on the shell 22. The positive electrode 81 is inserted into the first via 224, and the negative electrode 82 is inserted into the second via 225. An outer surface of the positive electrode 81 and an outer surface of the negative electrode 82 both form the outer surface of the electronic device 100. This facilitates contact of the charging electrode 8 with the external power supply, and facilitates electrical connection between the positive electrode 81 and the negative electrode 82 and the battery.

It may be understood that when the contact member is the charging electrode 8, one of the positive electrode 81 and the negative electrode 82 may be used as the contact member for heat conduction with the temperature sensor 4. Alternatively, both the positive electrode 81 and the negative electrode 82 may be used as the contact member for heat conduction with the temperature sensor 4, so that the area of contact between the contact member and the human skin can be increased.

The detection electrode 7 configured to detect the vital sign information may be configured to detect vital sign information of the human body. The detection electrode 7 may be electrically connected to the processor 301. After the detection electrode 7 detects vital sign information of a user, the vital sign information is processed by the processor and then displayed on the display 211b. In this way, the vital sign information of the user can be conveniently detected, so that a health status of the user can be conveniently monitored.

For example, in some embodiments of this application, the detection electrode 7 may be an electrocardiogram (electro cardio gram. ECG) electrode. In this way, electrocardiogram information of a user can be easily obtained, thereby facilitating monitoring of the health status of the user. Detection data of the ECG electrode is generated according to an electrical signal of the human skin acquired by the ECG electrode. The detection data of the ECG electrode is used for representing a potential difference between two limbs of the human body, for example, between a left upper limb and a right upper limb, between a left lower limb and the right upper limb, or between the left lower limb and the left upper limb. Since the detection electrode 7 has a relatively large area, using the detection electrode 7 as the contact member of the temperature sensor 4 can increase the area of contact between the contact member and the human skin, thereby improving the heat conduction efficiency between the contact member and the temperature sensor 4, and reducing a measurement error.

In this embodiment of this application, since the at least one of the charging electrode 8 and the detection electrode 7 of the electronic device 100 is used as the contact member of the temperature sensor 4, and the temperature of the human skin is transferred to the temperature sensor 4 through the charging electrode 8 or the detection electrode 7, the contact member for heat conduction with the temperature sensor 4 is not required to be additionally arranged when the electronic device 100 is provided with the charging electrode 8 or the detection electrode 7. In this way, a space occupied by the contact member is saved, thereby saving a space occupied in an overall design space of the electronic device 100. Therefore, more detection devices can be integrated on the electronic device 100 without increasing an area of the cover plate 22a, so that functions of the electronic device 100 are enriched. Moreover, holes required on the shell 22 can be reduced, thereby improving waterproof performance of the electronic device 100.

In some embodiments of this application, an impedance Z of the contact member satisfies: Z≤1Ω. Resistance to a current in a circuit with a resistance, an inductance, and a capacitance is referred to as an impedance. For example, the contact member may be a stainless steel member, a copper member, or the like. In this embodiment, by setting the impedance of the contact member to be less than 1Ω, when the contact member is the charging electrode 8 or the detection electrode 7, it is ensured that the temperature of the human skin can be quickly transferred to the temperature sensor 4, the sensitivity of the temperature sensor 4 and the accuracy of temperature measurement are improved, and signals of excellent quality of the charging electrode 8 or the detection electrode 7 are ensured.

In some embodiments, the detection electrode 7 includes a first electrode 71 and a second electrode 72. The first electrode 71 and the second electrode 72 are both arranged on the shell 22 and are spaced apart from each other. At least part of the first electrode 71 and at least part of the second electrode 72 are exposed from shell 22, and the part of the first electrode 71 exposed from shell 22 and the part of the second electrode 72 exposed from shell 22 define an annular structure. Since the first electrode 71 and the second electrode 72 are spaced apart from each other, the annular structure is a discontinuous annular structure with discontinuous parts. The annular structure may be a square annular shape, a circular annular shape, an elliptical annular shape, or the like. For example, referring to FIG. 5, the first electrode 71 and the second electrode 72 are both formed as an arcuate shape, and the first electrode 71 and the second electrode 72 are formed as a circular annular structure.

By arranging the first electrode 71 and the second electrode 72 as an annular structure, an area of contact between the first electrode 71 and the second electrode 72 and the human body can be increased. In addition, the annular structure can improve stability of the contact between the detection electrode 7 and the human body, thereby improving accuracy of a detection result of the detection electrode 7.

In addition, when the detection electrode 7 is an ECG electrode, that is, the first electrode 71 and the second electrode 72 are both the ECG electrode, if the first electrode 71 and the second electrode 72 are spaced apart from each other, common mode rejection (common mode rejection. CMR) performance of the ECG electrode can be improved. Therefore, anti-interference performance of the ECG electrode is improved, so that signal quality of the ECG electrode is further improved, and the detection result is more accurate. The common mode rejection means offsetting common mode signals on any two ends (input points of the two ends have a same phase) and amplifying a differential mode signal (a potential difference between the two ends).

Specifically, when the first electrode 71 and the second electrode 72 are both the ECG electrode, the detection electrode 7 further includes a third electrode 73. The third electrode is the ECG electrode. Exemplarily, referring to FIG. 6, the third electrode 73 may be arranged on the side frame 22b or the decorative ring 212. It may be understood that the first electrode 71 may be a positive ECG electrode, the second electrode 72 may be a driving electrode, and the third electrode 72 may be a negative ECG electrode.

For example, when the first electrode 71 is the positive ECG electrode and the third electrode 72 is the negative ECG electrode, after the user wears the electronic device 100 on one wrist, a skin of the wrist comes into contact with the cover plate 22a of the electronic device 100 to come into contact with the positive ECG electrode, and an other hand presses the side frame 22b or the decorative ring 212 to come into contact with the negative ECG electrode, so that a loop is formed between the human body and the electronic device 100. In this way. ECG detection data can be acquired. If the user wears the electronic device 100 on a left hand and presses the ECG electrode on the side frame 22b or the decorative ring 212 with a right hand, the left hand can come into contact with the positive ECG electrode, and the right hand can come into contact with the negative ECG electrode, so that a loop is formed between the human body and the electronic device 100. In this way, an electrical signal representing the potential difference between the left upper limb and the right upper limb can be acquired.

Referring to FIG. 6, the first electrode 71 includes a first body portion 711 and a first protruding portion 712, and the first protruding portion 712 is arranged on an inner surface of the first body portion 711. The second electrode 72 includes a second body portion 721 and a second protruding portion 722, and the second protruding portion 722 is arranged on an inner surface of the second body portion 721. The "inner surface" of the first body portion 711 is a side surface of the first body portion 711 facing the accommodating space. The "inner surface" of the second body portion 721 is a side surface of the second body portion 721 facing the accommodating space.

A first embedding groove 221 and a second embedding groove 222 are provided on an outer surface of the cover plate 22a. The first embedding groove 221 has a first communication hole 221a in communication with the accommodating space, and the second embedding groove 222 has a second communication hole 222a in communication with the accommodating space. The first body portion 711 of the first electrode 71 is arranged in the first embedding groove 221, and the first protruding portion 712 of the first electrode 71 extends into the accommodating space through the first communication hole 221a. The second body portion 721 of the second electrode 72 is arranged in the second embedding groove 222, and the second protruding portion 722 of the second electrode 72 extends into the accommodating space through the second communication hole 222a. By providing the first embedding groove 221 and the second embedding groove 222, the first electrode 71 and the second electrode 72 can be conveniently assembled on the shell 22, and the positions of the first electrode 71 and the second electrode 72 are more stable. In addition, by providing the first communication hole 221a in the first embedding groove 221 and the second communication hole 222a in the second embedding groove 222, electrical connection between the first electrode 71 and the second electrode 72 and the circuit board 3 can be conveniently realized.

Further, the first electrode 71 and the second electrode 72 are arranged axisymmetrically with respect to a central axis of the main body 2 in the X-axis direction or a central axis in the Y-axis direction. In this way, the first electrode 71 and the second electrode 72 can be distributed more uniformly, thereby further enhancing stability of the contact between the detection electrode 7 and the user, so that the detection result is more accurate. In addition, an appearance of the electronic device 100 is improved.

In some embodiments, the positive electrode 81 and the negative electrode 82 of the charging electrode 8 are arranged on an extending path of the annular structure or an extended line of the extending path. By arranging the positive electrode 81 and the negative electrode 82 of the charging electrode 8 on the extending path of the annular structure, the space of the shell 22 can be properly used, so that the overall layout of the electronic device 100 is more proper. Therefore, the charging electrode 8 and the detection electrode 7 both can be integrated on the shell 22, so that the functions of the electronic device 100 are more abundant and diverse.

In some embodiments, referring to FIG. 5 and FIG. 6, the first electrode 71 has a first end 71a and a second end 71b, and the second electrode 72 has a third end 72a and a fourth end 72b. The first end 71a of the first electrode 71 and the third end 72a of the second electrode 72 are opposite to and spaced apart from each other to form a first spacer region 226, and the second end 71b of the first electrode 71 and the fourth end 72b of the second electrode 72 are opposite to and spaced apart from each other to form a second spacer region 227. The first spacer region 226 and the second spacer region 227 are arranged on the extended line of the above extending path.

One of the positive electrode 81 and the negative electrode 82 of the charging electrode 8 may be arranged in the first spacer region 226, and the other of the positive electrode 81 and the negative electrode 82 of the charging electrode 8 may be arranged in the second spacer region 227. Certainly, the positive electrode 81 and the negative electrode 82 of the charging electrode 8 both may be arranged in the first spacer region 226 or the second spacer region 227. Therefore, a space between the first electrode 71 and the second electrode 72 can be fully used to arrange the charging electrode 8, so that the space of the shell 22 is fully and properly used, and a machining process of the first electrode 71 and the second electrode 72 is simplified, thereby improving machining efficiency.

Figure 10:
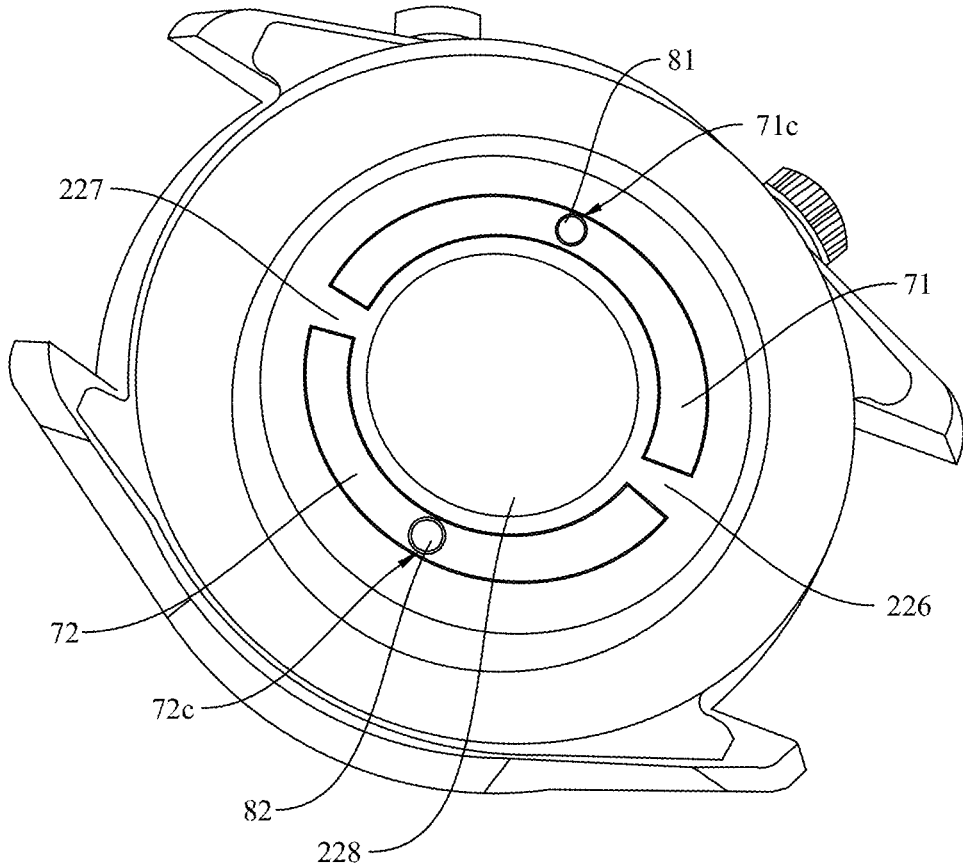
FIG. 10 is a schematic structural diagram of a main body of an electronic device according to still other embodiments of this application.

In some other embodiments, referring to FIG. 10. FIG. 10 is a perspective view of a main body 2 of an electronic device 100 according to some other embodiments of this application. A difference between a structure of the main body 2 of the electronic device 100 shown in FIG. 10 and the main body 2 of the electronic device 100 shown in FIG. 5 is that in the example of FIG. 10, the positive electrode 81 and the negative electrode 82 are arranged on the extending path of the annular structure.

Referring to FIG. 10, a first avoidance hole 71c is provided on the first electrode 71, and a second avoidance hole 72c is provided on the second electrode 72, so that the positive electrode 81 and the negative electrode 82 can be respectively arranged in the first avoidance hole 71c and the second avoidance hole 72c. In this way, the space of the shell 22 can be properly used, so that the overall layout of the electronic device 100 is more proper. Therefore, the charging electrode 8 and the detection electrode 7 both can be integrated on the shell 22, so that the functions of the electronic device 100 are more abundant and diverse.

In some embodiments of this application, referring to FIG. 2. FIG. 5, and FIG. 10, the electronic device 100 further includes a photoplethysmography (photo plethysmography. PPG) detection device, and a detection light window 228 of the PPG detection device is arranged on an inner side of the annular structure. The PPG detection device is configured to detect a PPG signal of a to-be-tested object, and can obtain health data such as a pulse of the to-be-tested object. The detection light window 228 is a light-transmissive formed on the shell 22. For example, light-transmissive glass may be arranged on the inner side of the annular structure to form the detection light window 228. Light emitted by the PPG detection device can be irradiated to a surface of the human skin through the detection light window 228, and reflected light after the light irradiated on the surface of human skin is absorbed by human blood and a muscle tissue 400 and the is received by the PPG detection device through the detection light window 228.

The PPG detection device is an infrared non-destructive detection technology, which detects, by using a photoelectric sensor, a different intensity of reflected light after absorption by human blood and a muscle tissue 400, and traces a variation of a blood vessel volume during a cardiac cycle, so as to obtain a pulse waveform and then calculate a heart rate.

Figure 11:
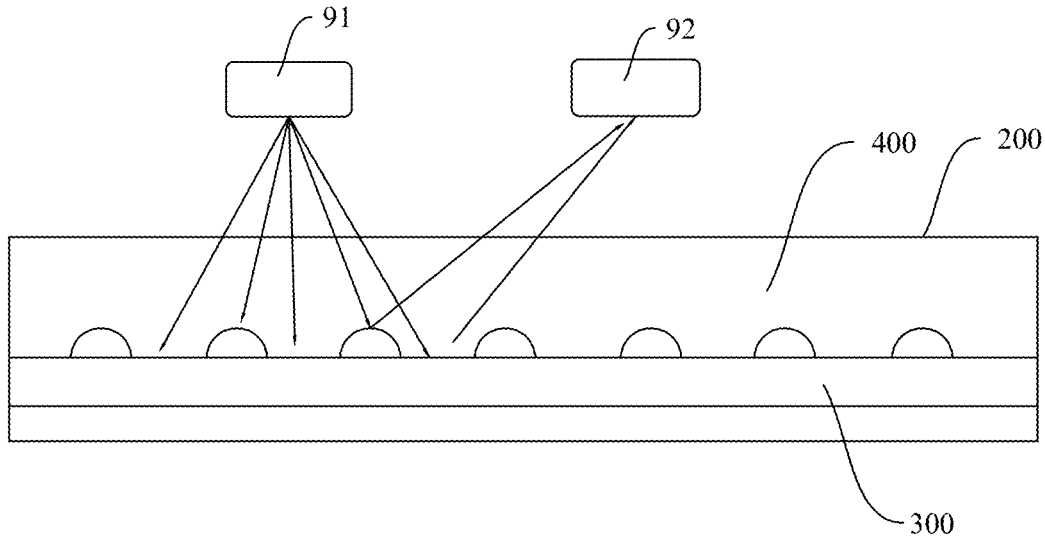
FIG. 11 is a schematic diagram of a detection process performed by a PPG detection device according to some embodiments of this application.

FIG. 11 is a schematic diagram of a detection process performed by the PPG detection device. Referring to FIG. 11, the PPG detection device includes a light-emitting element 91 and a light detector 92. The light-emitting element 91 and the light detector 92 may be arranged in the accommodating space and are electrically connected to the processor, and the light-emitting element 91 and the light detector 92 are both opposite to the detection light window 228.

In this way, when the light-emitting element 91 emits a light beam of a certain wavelength, the light beam can be irradiated to the surface of the human skin (for example, the wrist skin) through the detection light window 228. Contraction and expansion of blood vessels affect transmission or reflection of light during each heartbeat. When the light passes through a skin tissue 200 and is reflected to the light detector 92 by the detection light window 228, the light attenuates to a certain extent. Absorption of light by a muscle tissue 400, bones, veins and other connecting tissues substantially does not vary (if there is no large movement of a to-be-measured site), but absorption of light by an artery 300 varies. This is because there is blood pulsation in the artery 300. Therefore, the light absorption certainly varies. Therefore, after the light detector 92 converts an optical signal reflected and/or transmitted by a human body to an electrical signal, since the absorption of the light signal by the artery 300 varies and the absorption of the light signal by the other tissues substantially does not vary, the obtained signals may be classified into a direct current DC signal and an alternating current AC signal. By extracting the AC signal, characteristics of blood flowing can be learned, so that the pulse waveform can be obtained, and the heart rate can be calculated. It may be understood that a blood pressure value may be further calculated by using the detection data of the PPG detection device and the detection data of the ECG electrode 73.

By arranging the detection light window 228 of the PPG detection device on the inner side of the above annular structure, the space of the shell 22 can be properly used, so that the overall structure of the electronic device 100 is more compact. Therefore, the detection light window 228 of the PPG detection device, the ECG electrode 73, the charging electrode 8, and the contact member of the temperature sensor 4 can all be integrated on the cover plate 22a of the electronic device 100 without increasing the area of the cover plate 22a, so that the electronic device 100 can synchronously detect PPG detection data. ECG detection data, and body temperature detection data of a user, thereby obtaining data of the user reflecting a health status, such as a pulse, a heart rate, a blood pressure, and an electrocardiogram. In addition, the electronic device can determine emotion and tension of the user according to the ECG detection data and the body temperature detection data, thereby monitoring the health status of the user more comprehensively.

In some embodiments, an area of the detection light window 228 is substantially the same as an area of the inner side of the annular structure. In this way, a detection area of the detection light window 228 can be increased, thereby ensuring that the light of the PPG detection device is not blocked, and improving detection accuracy of the PPG detection device.

The electronic device 100 provided in this application may be worn on a wrist, or may be placed on a forehead, an armpit, or the like, and comes into contact with a human skin by using a contact member, so as to realize temperature detection of the human body. Specifically, when a user performs temperature detection by using the electronic device 100, a body temperature may be detected in real time by the electronic device 100. For example, the body temperature may be detected at a predetermined interval to monitor the body temperature in real time. The above predetermined time may be 1 min. 3 min. 5 min. 10 min. 30 min. 60 min. or the like. The user may adjust the predetermined time according to actual requirements. This is not limited in this application. Alternatively, the user may manually activate a temperature detection function by triggering a start switch, to realize detection of the temperature of the human body.

In the descriptions of this specification, the described specific features, structures, materials, or characteristics may be combined in a proper manner in any one or more of the embodiments or examples.

Finally, it should be noted that: the foregoing embodiments are merely used for describing the technical solutions of this application, but are not intended to limit this application. Although this application is described in detail with reference to the foregoing embodiments, a person of ordinary skill in the art should understand that, modifications may still be made to the technical solutions described in the foregoing embodiments, or equivalent replacements may be made to the part of the technical features; and such modifications or replacements will not cause the essence of corresponding technical solutions to depart from the spirit and scope of the technical solutions in the embodiments of this application.

What is claimed is:

1. An electronic device, characterized by comprising:
a shell, having an accommodating space;
a contact member, arranged on the shell, wherein at least part of a surface of the contact member forms an outer surface of the electronic device;
a temperature sensor, arranged in the accommodating space and having a positive electrode and a negative electrode; and
a circuit board, arranged in the accommodating space and provided with a positive wire and a negative wire, wherein
  the positive wire is connected to the positive electrode of the temperature sensor;
  the negative wire is connected to the negative electrode of the temperature sensor;
  at least one of the positive wire and the negative wire is thermally conductively connected to the contact member;
  the temperature sensor is configured to perform temperature measurement according to a temperature transferred from the at least one of the positive wire and the negative wire;
  the contact member and the temperature sensor are arranged on two opposite sides of the circuit board;
  the circuit board comprises a multi-layer wire structure formed by a metal layer and insulating dielectric layers that are alternately arranged in sequence;
  the positive wire comprises a positive wire body and a first metallized via, the positive wire body is formed on the metal layer, the first metallized via extends through surfaces on the two opposite sides of the circuit board, and the positive wire body is electrically connected to the first metallized via; and
  the negative wire comprises a negative wire body and a second metallized via, the negative wire body is formed on the metal layer, the second metallized via extends through the surfaces on the two opposite sides of the circuit board, and the negative wire body is electrically connected to the second metallized via.

2. The electronic device according to claim 1, wherein a thermal conductivity k1 of the contact member satisfies: $k1 \geq 15$ W/m·K.

3. The electronic device according to claim 1, wherein a thermal conductivity k2 of the at least one of the positive wire or the negative wire satisfies: $k2 \geq 10$ W/m·K.

4. The electronic device according to claim 1, further comprising a thermal insulator wrapped around at least part of an outer surface of the temperature sensor.

5. The electronic device according to claim 1, wherein
at least one of the first metallized via and the second metallized via is thermally conductively connected to the contact member.

6. The electronic device according to claim 5, wherein the positive wire further comprises a first positive pad and a second positive pad arranged opposite to each other on two ends of the first metallized via, and the first positive pad is electrically connected to the positive electrode of the temperature sensor;
  the negative wire further comprises a first negative pad and a second negative pad arranged opposite to each other on one end of the second metallized via, and the first negative pad is electrically connected to the negative electrode of the temperature sensor; and
  at least one of the second positive pad and the second negative pad is thermally conductively connected to the contact member.

7. The electronic device according to claim 1, further comprising:
  a charging electrode and a detection electrode configured to detect vital sign information, wherein the charging electrode and the detection electrode are arranged on the shell;
  at least part of a surface of the charging electrode and at least part of a surface of the detection electrode form the outer surface of the electronic device; and
  at least one of the charging electrode and the detection electrode forms the contact member.

8. The electronic device according to claim 7, wherein an impedance Z of the contact member satisfies: $Z \leq 1\Omega$.

9. The electronic device according to claim 7, wherein
  the detection electrode comprises a first electrode and a second electrode;
  the first electrode and the second electrode are both arranged on the shell and are spaced apart from each other;
  at least part of the first electrode and at least part of the second electrode are exposed from the shell; and
  the part of the first electrode exposed from the shell and the part of the second electrode exposed from the shell define an annular structure.

10. The electronic device according to claim 9, wherein the charging electrode comprises the positive electrode and the negative electrode arranged on an extending path of the annular structure or on an extended line of the extending path.

11. The electronic device according to claim 9, further comprising:
  a photoplethysmography detection device, wherein a detection light window of the photoplethysmography detection device is arranged on an inner side of the annular structure.

12. The electronic device according to claim 7, wherein the detection electrode is configured to detect an electrocardiogram electrode of an electrocardiogram.

13. The electronic device according to claim 1, wherein
the shell comprises a cover plate, a protruding portion
protruding away from a center of the accommodating
space is arranged on the cover plate; and
the contact member is arranged on the protruding portion.

* * * * *